United States Patent
Ruckh

(10) Patent No.: US 10,292,734 B1
(45) Date of Patent: May 21, 2019

(54) MICRO-STRUCTURES WITH MAGNETIC REMOVAL CAPABILITY AND OPTIONALLY CLEAR OPTICAL PATH

(71) Applicant: Verily Life Sciences LLC, Mountain View, CA (US)

(72) Inventor: Timothy Ruckh, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 386 days.

(21) Appl. No.: 14/685,760

(22) Filed: Apr. 14, 2015

Related U.S. Application Data

(60) Provisional application No. 62/068,110, filed on Oct. 24, 2014.

(51) Int. Cl.
*A61M 37/00* (2006.01)
*A61B 17/52* (2006.01)
*A61B 17/00* (2006.01)

(52) U.S. Cl.
CPC .......... *A61B 17/52* (2013.01); *A61M 37/0015* (2013.01); *A61B 2017/00876* (2013.01)

(58) Field of Classification Search
CPC .......... A61B 17/52; A61B 2017/00876; A61M 37/0015; A61M 2037/0023; A61M 2037/003; A61M 2037/0038; A61M 2037/0046; A61M 2037/0053; A61M 2037/0061
See application file for complete search history.

(56) References Cited

U.S. PATENT DOCUMENTS

| | | | |
|---|---|---|---|
| 6,334,856 B1 * | 1/2002 | Allen ................. | A61B 5/14514 128/898 |
| 8,137,736 B2 | 3/2012 | Zhu et al. | |
| 2002/0082543 A1 * | 6/2002 | Park .................... | A61B 5/1411 604/21 |
| 2008/0108959 A1 * | 5/2008 | Jung ................. | A61M 37/0015 604/272 |
| 2008/0125743 A1 * | 5/2008 | Yuzhakov ......... | A61M 37/0015 604/506 |
| 2011/0224515 A1 * | 9/2011 | Mir .................... | A61B 5/14532 600/317 |
| 2011/0306853 A1 * | 12/2011 | Black .................. | A61B 5/1468 600/309 |

(Continued)

*Primary Examiner* — Carrie R Dorna
(74) *Attorney, Agent, or Firm* — McDonnell Boehnen Hulbert & Berghoff LLP

(57) ABSTRACT

Systems and methods are described that may provide an efficient way to retrieve microneedles from tissue. For example, magnetic material may be incorporated into one or more microneedles. The microneedles may be delivered to a region of tissue via a backing material, such as a transdermal patch. The microneedles may provide therapeutic drug delivery and/or diagnostic information about the tissue or, more generally, the body containing the tissue. To retrieve the microneedles, a retrieval magnet may apply a magnetic field to the region of tissue where the microneedles were delivered. The magnetic field may attract the microneedles to aid in extraction of the microneedles from the tissue. In some embodiments, an excitation light source and light sensor may be included in the system and method to determine whether the microneedles were retrieved from the tissue.

25 Claims, 10 Drawing Sheets

(56) References Cited

U.S. PATENT DOCUMENTS

| | | |
|---|---|---|
| 2013/0165772 A1 | 6/2013 | Traverso et al. |
| 2013/0218083 A1 | 8/2013 | Yuzhakov |
| 2014/0066855 A1 | 3/2014 | Luttge et al. |
| 2014/0148669 A1* | 5/2014 | Garcia Saban .... A61B 5/14532 600/347 |
| 2014/0330209 A1 | 11/2014 | Frederickson et al. |

* cited by examiner

MICRO-STRUCTURES WITH MAGNETIC REMOVAL CAPABILITY AND OPTIONALLY CLEAR OPTICAL PATH

CROSS-REFERENCE TO RELATED APPLICATIONS

This application is a nonprovisional of U.S. Provisional Patent Application Ser. No. 62/068,110 filed Oct. 24, 2014, the contents of which are hereby incorporated by reference.

BACKGROUND

Microneedle arrays have been developed as an alternative to needle and syringe injections. Such arrays have been used as drug delivery devices, offering the potential of less pain and bleeding at the application site as well as specific penetration depths.

In addition to delivering drug therapies, microneedle arrays may additionally offer new ways in which to read information from embedded or implanted bio-sensors. For example, a multiplicity of individual microneedle probes may provide a corresponding array of access points to make and read measurements from a biological system.

SUMMARY

In a first aspect, a system is provided. The system includes a microneedle, a retrieval magnet, and a controller. The microneedle is configured to be embedded in skin tissue and includes a magnetic material. The controller includes at least one processor and is programmed to carry out operations. The operations include after the microneedle is embedded in the skin tissue, causing the retrieval magnet to apply a magnetic field to the microneedle embedded in the skin tissue. The magnetic field is sufficient to retrieve the microneedle from the skin tissue. The operations include receiving a signal indicative of retrieval of the microneedle from the skin tissue.

In a second aspect, a method is provided. The method includes controlling, by a computing device, a retrieval magnet to apply a magnetic field to a microneedle embedded in skin tissue. The microneedle includes a magnetic material and the magnetic field is sufficient to retrieve the microneedle from the skin tissue. The method also includes receiving, by the computing device, a signal indicative of retrieval of the microneedle from the skin tissue. The method additionally includes controlling, by the computing device, the retrieval magnet to remove the magnetic field from the skin tissue in response to receiving the signal.

In a third aspect, a method is provided. The method includes embedding a plurality of microneedles in skin tissue. The microneedles are detachably coupled to a backing material and the microneedles include a magnetic material. The method also includes detaching the backing material from the plurality of microneedles embedded in the skin tissue. The method additionally includes controlling, by a computing device, a retrieval magnet to apply a magnetic field to the plurality of microneedles embedded in the skin tissue. The magnetic field is sufficient to retrieve the plurality of microneedles from the skin tissue. The magnetic field may optionally assist in the implantation of microneedles into the skin. The method further includes receiving, by the computing device, a signal indicative of retrieval of the plurality of microneedles from the skin tissue. The method yet further includes controlling, by the computing device, the retrieval magnet to remove the magnetic field from the skin tissue in response to receiving the signal.

In a fourth aspect, a device is provided. The device includes a microneedle configured to be embedded in skin tissue. The microneedle includes a magnetic material. The microneedle is also configured to be extracted from the skin tissue by way of an applied magnetic field.

Other aspects, embodiments, and implementations will become apparent to those of ordinary skill in the art by reading the following detailed description, with reference where appropriate to the accompanying drawings.

DETAILED DESCRIPTION

Figure 1A:
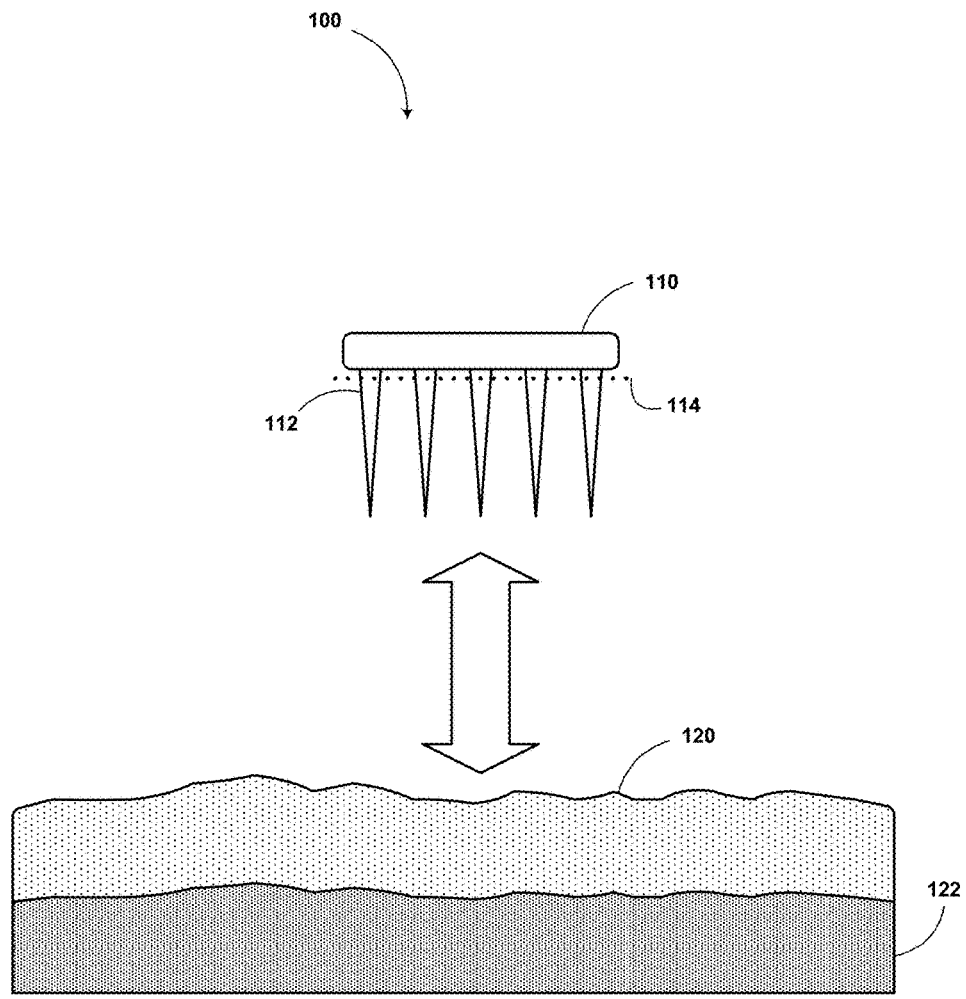
FIG. 1A illustrates a microneedle system, according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where implantation and retrieval of microneedles is desired. The environment may include any living or non-living body or a portion thereof. The environment may include non-human tissues. For example, one of skill in the art will recognize that the embodiments disclosed herein may be applied generally to retrieve microneedles in many different contexts. Yet further, while the present disclosure may describe microneedles as an example structure, other structures and geometries, such as nanoparticles, macro particles, etc. are possible. For example, the magnetic retrieval of a particle that incorporates a therapeutic drug and a magnetic material is contemplated within the scope of this application. Moreover, while the present disclosure describes embodiments for use in vivo, one of skill in the art will also recognize that in vitro applications are possible as well.

Overview

In an embodiment, a system and a method for its use may include one or more microneedles, which may be used for drug delivery and/or medical diagnostic purposes. The system and method may include the deployment of the microneedles into tissue, such as into tissues within a human body. The microneedles may include a magnetic material. The system and method may further include retrieval of the microneedles from the tissue using a retrieval magnet. The system and method may include a way to determine whether the microneedles have been retrieved from the tissue. In some embodiments, the system and methods for its use may help to improve the feasibility, safety, and efficacy of drug delivery and medical diagnostic techniques that utilize microneedles.

The microneedles may be coated with the magnetic material. Alternatively, the magnetic material may be incorporated into the microneedles. For example, the microneedles may be formed, at least in part, from a hydrogel. Magnetic nanoparticles may be incorporated into the hydrogel. The magnetic material may include magnetic nanoparticles, iron oxide, ferrite, rare earth materials, and/or other magnetic materials.

The microneedles may initially be coupled to a common substrate or backing material. The backing material may be, for example, a dissolvable transdermal patch. Alternatively or additionally, the backing material may include polyvinyl alcohol (PVOH or PVA), dextran, hyaluronan, chitosan, or another water-soluble polymer. Other bio-degradable and bio-compatible materials are contemplated for use as the backing material. Alternatively, the backing material may be non-dissolvable.

The microneedles may be delivered to a particular portion of skin tissue. The skin tissue may be a portion of a human body. The microneedles may be delivered by pressing the backing material, which includes the microneedles, against the skin tissue so as to embed the microneedles in the skin tissue. The embedded microneedles may extend through the epidermis to an underlying capillary bed in the dermis layer of skin tissue.

In an example embodiment, the microneedles may be between 50-1000 microns in length, although other lengths are possible. Other non-needle structures may range from 2 microns up to 1000 microns.

After the microneedles have been embedded in the skin tissue, the backing material may optionally be detached from the microneedles. In an example embodiment, the backing material may be peeled away from the microneedles. Alternatively, the backing material may remain attached to the microneedles until it dissolves away. For example, the backing material may be dissolved using water or alcohol.

Once delivered, the microneedles may be configured to deliver a dosage of a therapeutic drug. For example, the microneedles may be formed, at least in part, from a hydrogel. Nanoparticles incorporated into the hydrogel may act as drug delivery devices. Additionally or alternatively, diffusion of various active pharmaceutical ingredients from the microneedles is possible.

Additionally or alternatively, the microneedles may be configured to provide diagnostic information via optical means. For example, the microneedles may include an optode or another type of chemical sensor configured to change its optical properties while in proximity to a particular analyte. In such an example, the optode may be illuminated by an excitation light source. In response to receiving light at the excitation wavelength, certain materials such as fluorophores in the optode may usually emit emission light. When in proximity of the specific analyte, the emission behavior may be quenched or otherwise attenuated or else increased. Embodiments may also contain a combination of optical materials such that one material increases the strength of its optical signal while one other material decreases the strength of its optical signal. In this way, the microneedles may be used to detect a concentration, presence, or lack thereof of a particular analyte.

In some example embodiments, the microneedles and their associated magnetic particles may be used to produce or modulate a local magnetic field. For example, an array of magnetic microneedles embedded in tissue may form a magnetic field with periodic variations due, at least in part, from the microneedle spacing. A change in the magnetic field may be indicative of a presence of a particular analyte or marker. Accordingly, diagnostic information may be obtained by monitoring the magnetic field produced by the embedded microneedles using magneto-optical devices, for example.

The retrieval magnet may include a permanent magnet and/or an electromagnet. In some embodiments, the retrieval magnet may be operable to provide a constant magnetic field. In other embodiments, the retrieval magnet may be operable to provide a pulsed, variable, and/or switchable magnetic field.

The magnetic field from the retrieval magnet may be applied to the skin tissue in which the microneedles have been embedded. In one approach, a permanent magnet may be positioned in close proximity to the skin tissue. In another approach, an electromagnet may be turned on while in proximity to the skin tissue. In either approach, a controller may cause the retrieval magnet to apply a magnetic field to the microneedle embedded in the skin tissue, such as by moving a permanent magnet or electromagnet into proximity to the skin tissue and/or by applying current to an electromagnet. The magnetic field may be sufficient so as to physically extract the microneedle from the skin tissue. For example, the magnetic material associated with the microneedles may be attracted by the magnetic field generated by the retrieval magnet. In such a scenario, the microneedle may be physically pulled out of the skin based on this magnetic attraction.

After retrieving the microneedles from the skin, a signal may be received. The signal may be indicative of retrieval of the microneedle from the skin tissue. For example, an excitation light source may illuminate a surface of the retrieval magnet with excitation light at an excitation wavelength. Upon retrieving the microneedle, a material in the microneedle, such as a fluorophore, may emit fluorescence light at an emission wavelength in response to receiving the excitation light at the excitation wavelength. Accordingly, a light sensor configured to detect light at the emission wavelength may transmit the signal to the controller. In turn, the controller may cause the retrieval magnet to remove the magnetic field from the skin tissue. For example, in the case that the retrieval magnet is an electromagnet, the controller may turn off the current being applied to the electromagnet. In the case that the retrieval magnet is a permanent magnet, the controller may move the permanent magnet away from the skin tissue.

The controller may include a computer having a processor and a memory. The controller may take other forms as well. For example, the controller may include a distributed computing system or a cloud-based server network. Alternatively or additionally, the controller may be a mobile device. The controller may include software, such as hardware drivers and/or application programming interfaces, configured to control the aforementioned elements of the system. The controller may communicate with and/or control some or all of the other elements of the system using wireless communications.

Retrieval of microneedles using the described systems and methods may improve the safety and efficacy of this type of medical device and provide a means to reliably terminate drug dosage or physiological diagnostic methods.

System Examples

FIG. 1A illustrates a system 100, according to an embodiment. The system 100 may include a backing material 110 and one or more microneedles 112. The backing material 110 may include a dissolvable, bio-degradable, and/or bio-compatible material. The microneedles 112 include a magnetic material.

The microneedles 112 may be configured to be embedded in the epidermis 120 and the dermis 122 layers of skin tissue. In some embodiments, the microneedles 112 may be 50-1000 microns in length. However, other microneedle lengths are possible. The microneedles 112 may include materials such as a hydrogel, a metal, one or more polymers, and/or a plastic. Other materials are possible.

The microneedles 112 include one or more known magnetic materials. For example, a microneedle 112 may be formed, at least in part, by a hydrogel. The hydrogel may incorporate magnetic nanoparticles, such as iron oxide ($Fe_3O_4$), cobalt iron oxide ($CoFe_2O_4$), iron cobalt (FeCo), iron platinum (FePt), etc. Other magnetic materials may be incorporated into the microneedles 112. For instance, alnico, ferrite, nickel, rare earth materials, and other magnetic materials are contemplated herein.

The magnetic materials may be incorporated into the microneedles 112 in different positions. In an example embodiment, the microneedle may include a tip portion and a base portion. In such an embodiment, the magnetic material may be disposed near the base portion. For example, the magnetic material may be deposited around the base of the microneedles 112.

The microneedles 112 may be configured to provide delivery of a therapeutic drug. For example, in the case where the microneedles 112 include a hydrogel matrix, large and/or small molecules may be incorporated into the hydrogel. Once introduced into the skin tissue, the large and/or small molecules may diffuse out of the hydrogel matrix and into the body. A wide variety of therapeutic drugs are contemplated herein including those with an active pharmaceutical ingredient (API).

The microneedles 112 may be alternatively or additionally configured to provide physiological diagnostics. For example, the microneedles 112 may include an optode disposed proximate to the tip of the microneedle 112. The optode may include a fluorophore. In an example embodiment, the fluorophores may assist in the detection of particular analytes of interest in skin tissue and/or the interstitial fluid.

Fluorophores may absorb light of a particular wavelength and re-emit light at a longer emission wavelength as emission light. As contemplated herein, fluorophores may have excitation wavelengths in the red to near infrared wavelengths, but other excitation wavelengths are possible. The fluorophores may have corresponding emission wavelengths in the visible to near-infrared spectrum, but other emission wavelengths are possible. Some examples of fluorophore molecules include cell/tissue dyes, the active agent of which may include a small molecule, protein, or quantum dot. Some embodiments may involve energy transfer including, but not limited to, Förster resonance energy transfer (FRET), in which an excited electron of a first fluorophore (e.g. a donor dye) is passed to a second fluorophore (e.g. an acceptor dye), which may result in a reduced fluorescence from the first dye. The acceptor does not necessarily need to emit a photon in this case, though it may. Fluorophores may be incorporated in the microneedles 112. For example, the fluorophore may be incorporated into a hydrogel matrix. Alternatively, the fluorophores may be incorporated into optodes disposed proximate to the tips of the microneedles 112. Additionally or alternatively, one or more fluorophores may be incorporated into the epidermis 120, the dermis 122 and/or another fluorophore may be incorporated into other parts of the body, such as surrounding tissue, bone, body cavity, etc. Other combinations of fluorophores are possible and contemplated herein.

Although this disclosure specifically addresses the use of fluorophores as indicating a particular analyte of interest, other types of luminescence properties may be utilized for such purposes. For example, chemiluminescence and phosphorescence of tissues and various biomarkers may be utilized in association with the methods and devices disclosed herein.

Furthermore, other types of optical and/or plasmonic materials may be used in alternatively from or in addition to fluorophores. For example, plasmonic materials such as gold or silver nanoparticles and nanorods are contemplated within the scope of the present disclosure.

Figure 1B:
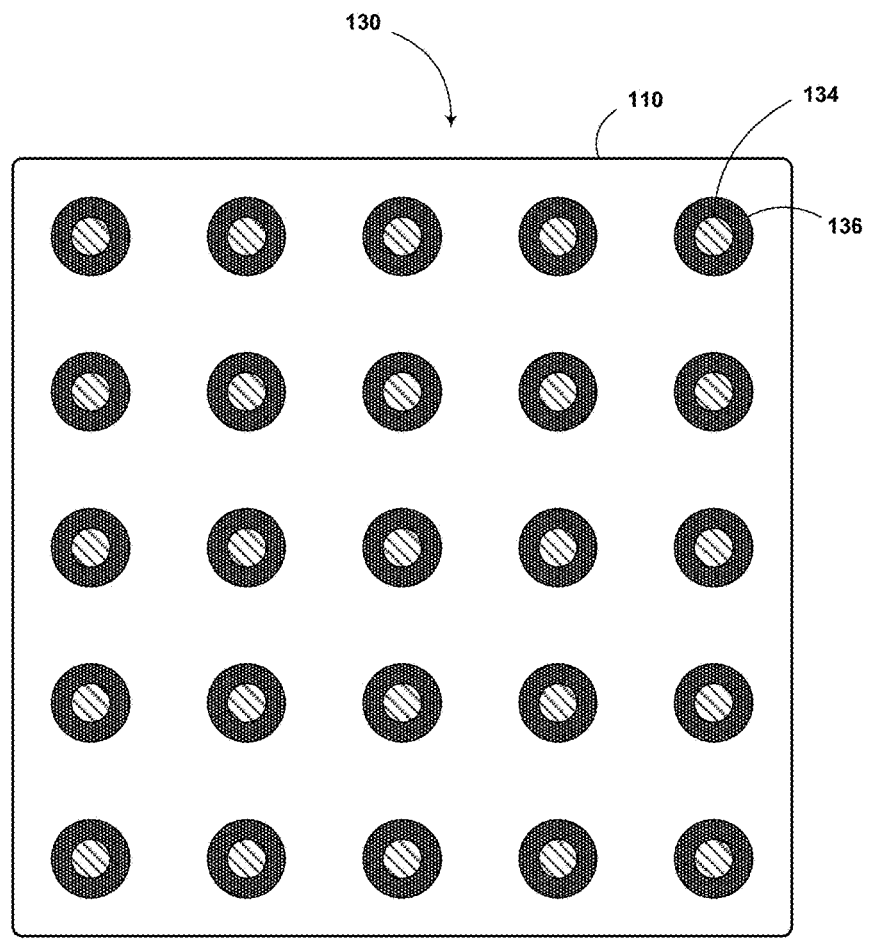
FIG. 1B illustrates a cross-section of a microneedle system, according to an example embodiment.

FIG. 1B illustrates a cross-section 130 of a microneedle system, according to an example embodiment. The cross-section 130 may include a view along plane 114 as illustrated in reference to FIG. 1A. Cross-section 130 includes a view of the backing material 110 as well as an array of microneedles. The microneedles may include a magnetic material 136 disposed around a microneedle core 134. The microneedle core 134 may include a hydrogel matrix. For example, the hydrogel matrix may include small molecules configured to provide a therapeutic drug dosage once introduced into skin tissue. Alternatively, the microneedle core 134 may include materials common to optical waveguides and/or optical fibers.

Figure 1C:
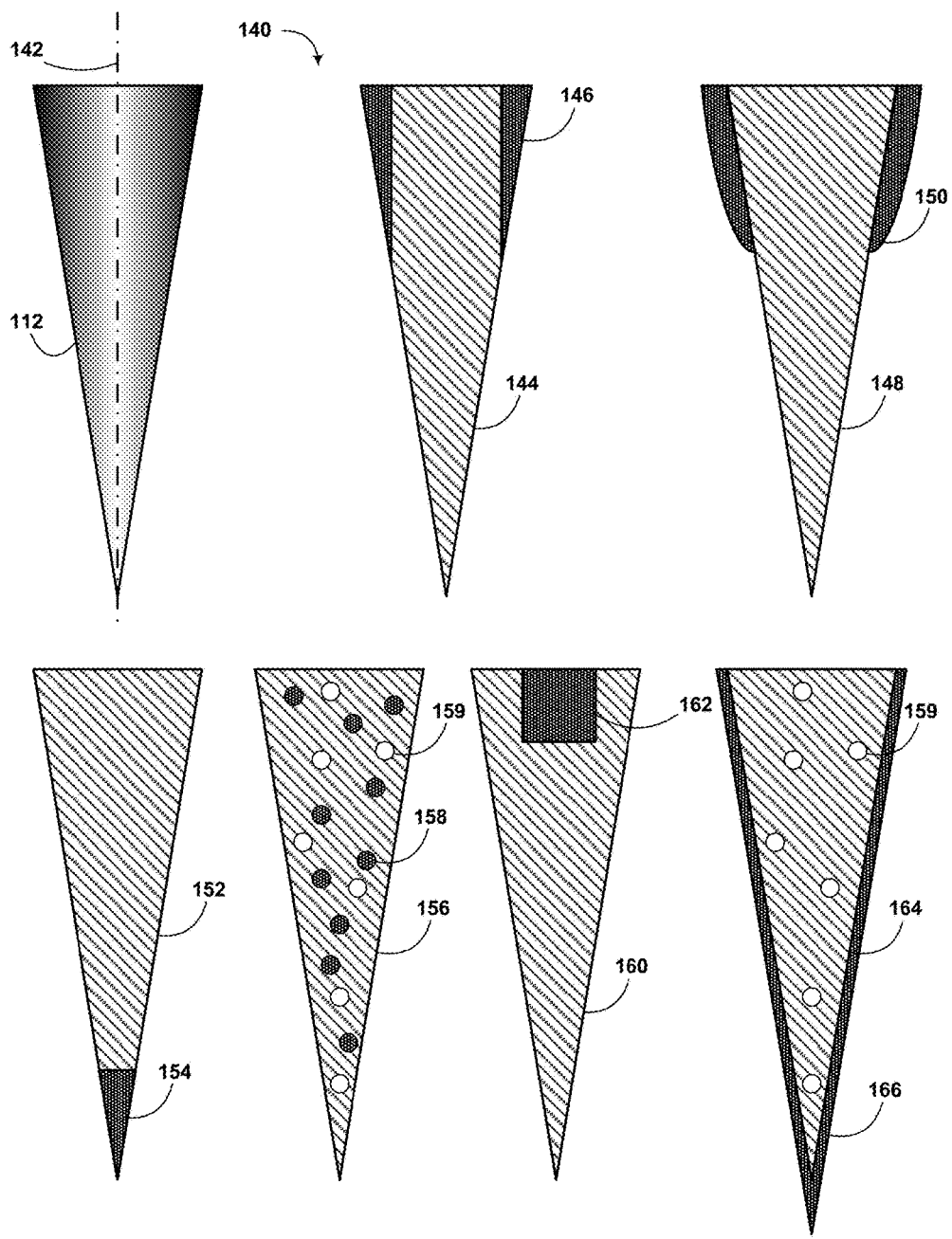
FIG. 1C illustrates several microneedles, according to example embodiments.

FIG. 1C illustrates several microneedles 140, according to example embodiments. Specifically, FIG. 1C illustrates the cross-sections of microneedles contemplated in various embodiments herein. The cross-sections are provided for views along a plane coincident with a central axis 142 of a microneedle 112.

Microneedle 144 includes a magnetic material 146 incorporated in a ring that is radially disposed about the base portion of the microneedle 144 and incorporated into the structure of the microneedle 144 (e.g., incorporated into microneedle 144 during its fabrication).

Microneedle 148 includes a magnetic material 150 which may be deposited around the base portion of the microneedle 148 after the microneedle 148 has been fabricated.

Microneedle 152 includes a magnetic material 154 incorporated into a tip portion of the microneedle 152.

Microneedle 156 includes a magnetic material 158 in the form of magnetic nanoparticles 158 dispersed within a hydrogel matrix. Other nanoparticles 159 may also be included in the hydrogel matrix. In some examples, the other nanoparticles 159 could include optodes configured to sense a particular analyte. In some examples, the other nanoparticles 159 could include a fluorophore that may be used to obtain a signal indicative of retrieval of the microneedle 156 (e.g., retrieval from skin tissue in which the microneedle 156 had been embedded).

Microneedle 160 includes a magnetic material 162 that is disposed at a central part of the base portion of the microneedle 160.

Microneedle 164 includes a magnetic material 166 that may be applied as a dip-coating or a deposited coating after microneedle 164 has been fabricated. Microneedle 164 may further include other nanoparticles 159 dispersed within a hydrogel matrix.

Although FIG. 1C illustrates certain example configurations of microneedles and corresponding magnetic material, it is to be understood that other configurations are possible and contemplated herein.

Figure 1D:
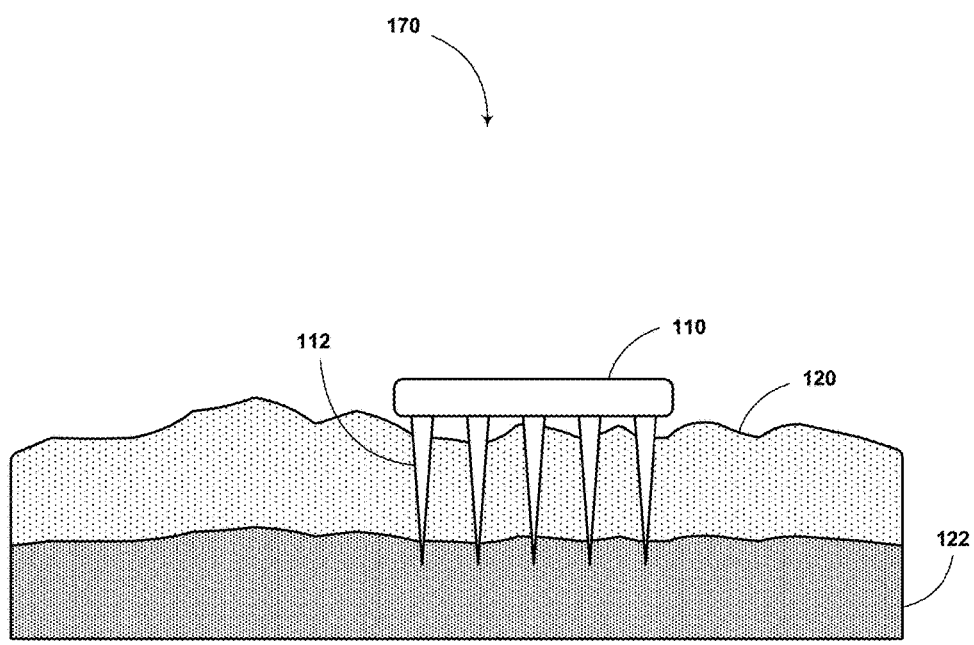
FIG. 1D illustrates a scenario involving a microneedle system, according to an example embodiment.

FIG. 1D illustrates a scenario involving a microneedle system 170, according to an example embodiment. In this scenario, the backing material 110 and microneedles 112 are applied together to the skin tissue. The application of pressure on the backing material 110 and/or microneedles 112 pushes the microneedles 112 through the epidermis layer 120 and into the dermis layer 122, to result in the configuration of embedded microneedles 112 shown in FIG. 1D. As shown, the embedded microneedles 112 extend through the epidermis layer 120 and into the dermis layer 122, such that at least a tip portion of the microneedles 112 is in contact with the dermis layer 122. Further, the base portions of the microneedles 112 are attached to the backing material 110 outside of the skin tissue.

Figure 1E:
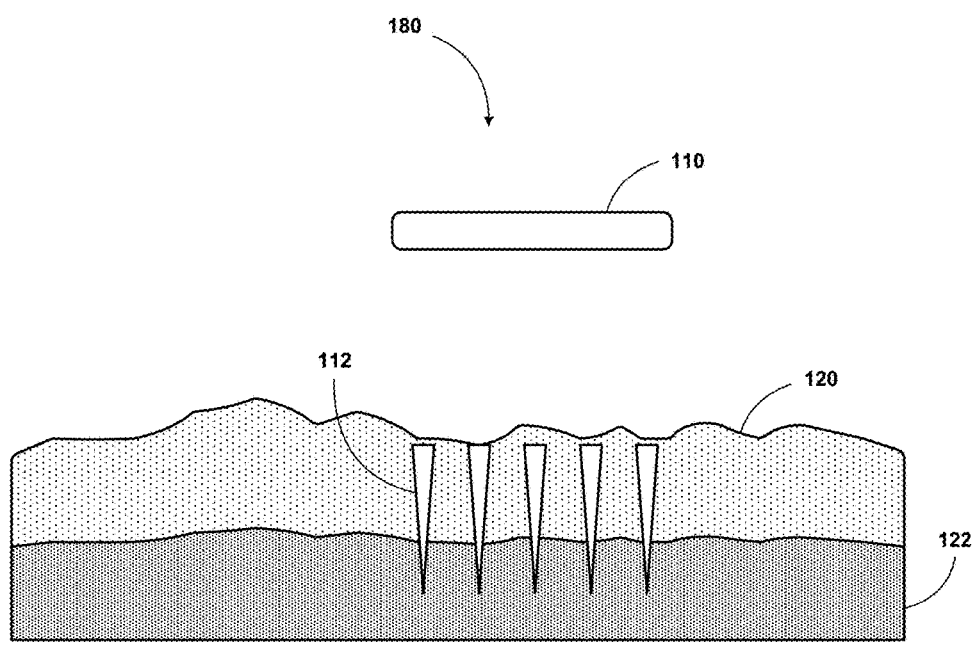
FIG. 1E illustrates a scenario involving a microneedle system, according to an example embodiment.

FIG. 1E illustrates a scenario involving a microneedle system 180, according to an example embodiment. As illustrated, the backing material 110 may be detachably removed from the microneedles 112, leaving the microneedles 112 embedded in the skin tissue. In some cases, the embedded microneedles 112 may be entirely within the skin tissue, as illustrated. In other cases, the embedded microneedles 112 may protrude from the surface of the skin tissue, such that a portion of the embedded microneedles 112 is within the skin tissue and a portion of the embedded microneedles 112 is outside of the skin tissue.

Figure 1F:
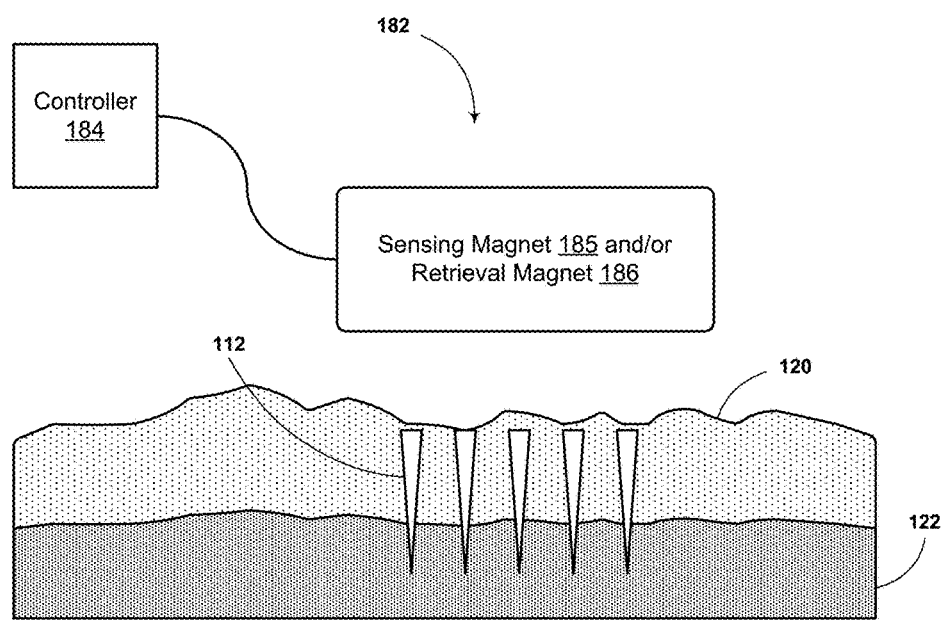
FIG. 1F illustrates a scenario involving a microneedle system, according to an example embodiment.

FIG. 1F illustrates a scenario involving a microneedle system 182, according to an example embodiment. System 182 may include a controller 184, a sensing magnet 185, and a retrieval magnet 186. The controller 184 may include a computer, which may in turn include a processor and memory. The sensing magnet 185 and retrieval magnet 186 may be permanent magnets and/or electromagnets. In some embodiments, the sensing magnet 185 and the retrieval magnet 186 may be the same magnet. Alternatively, the sensing magnet 185 and the retrieval magnet 186 may be different magnets.

The sensing magnet 185 may be configured to provide a sensing signal to the controller 184 based on an interaction with the microneedles 112. For example, the microneedles 112 may be configured to act as magnetic antennas for the sensing magnet 185. In such a scenario, the sensing magnet 185 may provide to the controller 184 a sensing signal, which may include information about the local environment of the microneedles 112.

In an example embodiment, a combination of the microneedles 112 and the sensing magnet 185 may operate as a Hall Effect sensor. That is, the sensing magnet 185 may act as a Hall plate and provided sensing signal may relate to a position of the microneedles 112 with respect to the sensing magnet 185. Other ways of operating the sensing magnet 185 and the microneedles 112 as a magnetic transducer are contemplated herein in an effort to provide information about the local environment of the microneedles 112.

In some embodiments, the controller 184 may be configured to execute operations. The operations may include receiving the sensing signal from the sensing magnet 185. As described above, the sensing signal may provide information about a local environment of the microneedles 112 and/or a location of the microneedles 112 with respect to the sensing magnet 185.

The operations may additionally include causing the retrieval magnet 186 to produce a magnetic field to the skin tissue. Namely, the magnetic field from the retrieval magnet 186 may act to attract the magnetic material incorporated within the microneedles 112.

Figure 1G:
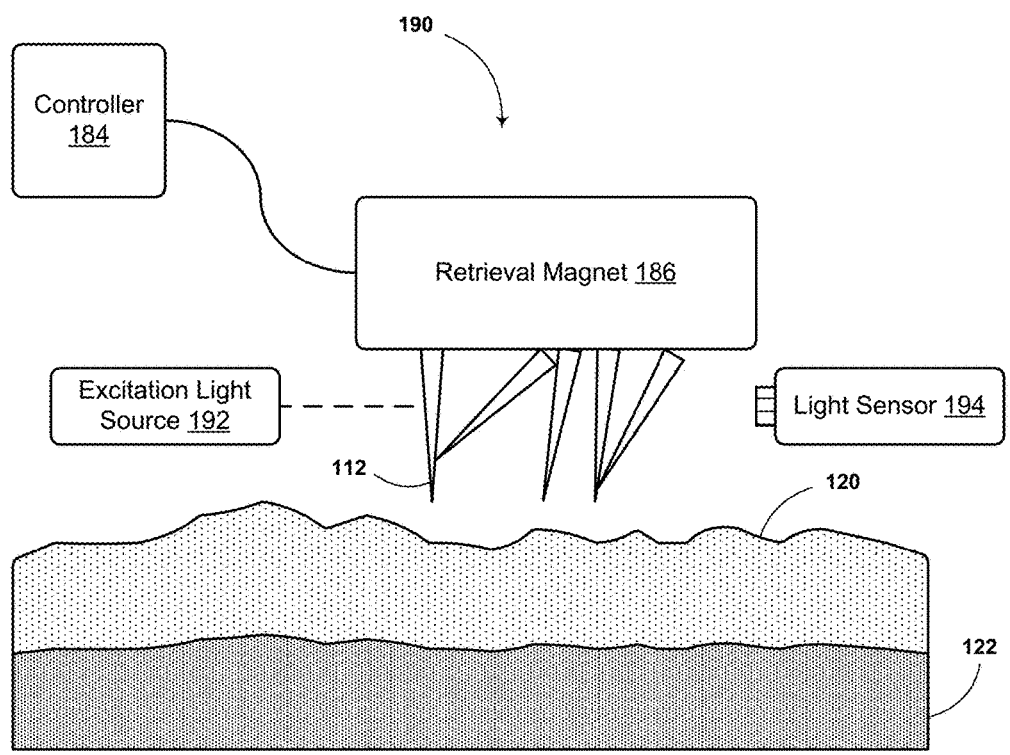
FIG. 1G illustrates a scenario involving a microneedle system, according to an example embodiment.

FIG. 1G illustrates a scenario involving a microneedle system 190, according to an example embodiment. In the illustrated scenario, microneedles 112 have been retrieved from the skin tissue 120 and 122 by the retrieval magnet 186. System 190 includes an excitation light source 192 configured to illuminate the microneedles 112 with excitation light that causes a fluorophore in the microneedles 112 to emit fluorescence light. The excitation light source 192 may include a laser, such as a helium neon (HeNe) laser. Alternatively, the excitation light source 192 may be a xenon or mercury lamp, a light emitting diode, or another light source configured to cause the fluorophore in the microneedles 112 to emit fluorescence light. In other words, the excitation light source 192 may produce light having a wavelength that corresponds to an excitation wavelength of the fluorophore. The excitation light may include, but is not limited to, light with wavelength range between 380 nanometers and 1.4 microns.

The system 190 may include a light sensor 194 configured to detect light at least at the emission wavelength of the fluorophore. Light sensor 194 may include a field of view. The field of view of light sensor 194 may include the skin tissue where the microneedles were deployed. Alternatively or additionally, field of view of the light sensor 194 may include at least one surface of the retrieval magnet 186.

The light sensor 194 may be a charge-coupled device (CCD) camera or another type of camera configured to capture images of the field of view so as to identify fluorophores emitting emission light at the emission wavelength. The light sensor 194 may be configured to detect light at only near the emission wavelength. Alternatively, the light sensor 194 may be configured to detect light within a relatively broad wavelength spectrum that encompasses the emission wavelength.

In another example embodiment, light sensor 194 may be configured to provide a close-up image of a surface of the retrieval magnet. The close-up image may undergo object recognition analysis in an effort to recognize whether the microneedles have been retrieved from the skin tissue. Other ways of determining whether the microneedles have been recaptured are possible.

Figure 2:
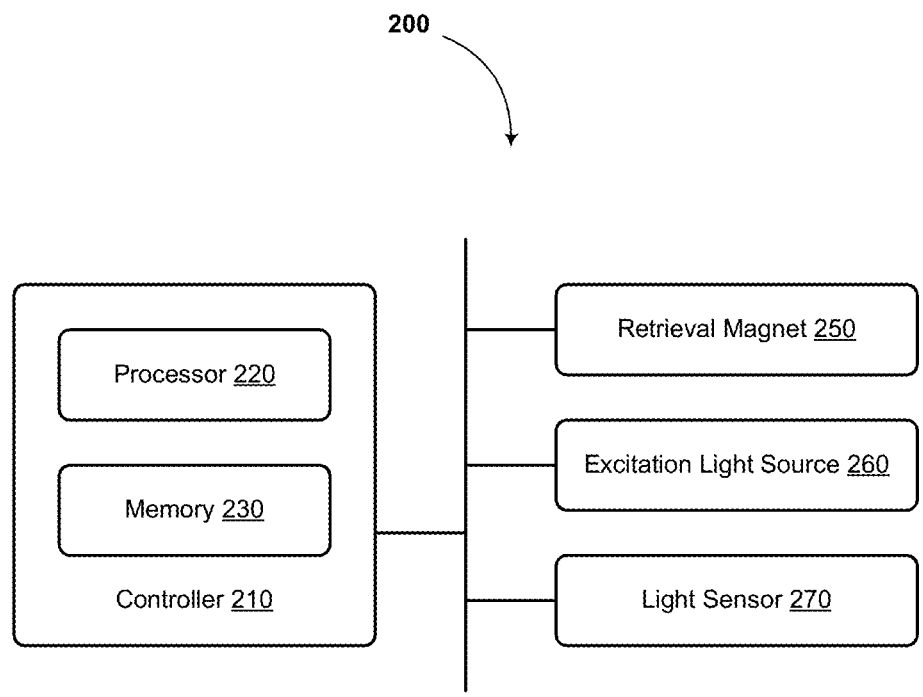
FIG. 2 illustrates a schematic block diagram of a system, according to an example embodiment.

FIG. 2 illustrates a schematic block diagram of a system 200, according to an embodiment. Elements of system 200 may be similar or identical to elements of any of the systems described and illustrated in reference to FIGS. 1A-1G. For example, FIG. 2 shows a controller 210, which may be similar or identical to the controller 184 shown in FIGS. 1F and 1G. The controller 210 may include a processor 220 and a memory 230. Memory 230 could be any type of non-transitory computer readable medium. The controller 210 may include a mobile device, a laptop computer, or another computing device. The controller 210 may include one or more computers. The computers need not be collocated, but may be distributed, for example, as part of a cloud server network.

System 200 may further include a retrieval magnet 250, an excitation light source 260, and a light sensor 270. The controller 210 may be able to communicate to each of the other elements of the system 200 via a communication bus. Alternatively or additionally, controller 210 may be able to communicate with one or more of the other elements of system 200 via direct wired and/or wireless communication links.

Program instructions may be stored in memory 230 and may be executable by processor 220. Such program instructions may include instructions that carry out or cause the elements of method 300 and method 400 as illustrated and described in reference to FIGS. 3 and 4. Namely, the program instructions may include controlling the retrieval magnet 250 to apply a magnetic field to a plurality of microneedles embedded in skin tissue. In particular, the magnetic field applied may be sufficient to retrieve the plurality of microneedles from the skin tissue. The program instructions may further include receiving a signal indicative of retrieval of the plurality of microneedles from the skin tissue. The program instructions may also include controlling the retrieval magnet to remove the magnetic field from the skin tissue in response to receiving the signal. Other program instructions are possible to carry out or cause actions described elsewhere herein.

As described herein, controller 210 may control and/or adjust parameters associated with one or more of the other elements of system 200. For example, controller 210 may cause the excitation light source 250 to produce excitation light. Furthermore, controller 210 may receive from light sensor 270 a signal indicative of the microneedles being removed from the skin tissue. In some embodiments, controller 210 may additionally cause the light sensor 270 to capture an image of a field of view that includes at least the particular tissue location and/or the retrieval magnet 250. In some embodiments, controller 210 may control other aspects of light sensor 270. For example, controller 210 may adjust the shutter speed or integration time, sensitivity (e.g. ISO), aperture, white balance, sensing wavelength, and/or other aspects of light sensor 270.

In an example embodiment, controller 210 may determine that the image of the retrieval magnet indicates light at an emission wavelength of a fluorophore. For example, controller 210 may analyze the image. The analysis may indicate that emission light at an expected emission wavelength is greater than a predetermined threshold (e.g. a minimum intensity). Under such conditions, the controller 210 may determine that the microneedles have been retrieved.

In response to determining the microneedles have been retrieved, the controller 210 may cause the retrieval magnet 250 to stop producing a magnetic field or move the retrieval magnet 250 away from the skin tissue. In other words, upon determining the microneedles have been recaptured, the controller 210 may be configured to remove the magnetic field from the skin tissue.

Controller 210 may also optionally adjust or control various other aspects of system 200. For example, controller 210 may be configured to adjust or control optical components that are configured to focus, direct, steer, adjust, reflect, or attenuate/absorb the light in system 200. For example, controller 210 may control a lens so as to obtain proper focus and/or direction of excitation light. For instance, controller 210 may adjust neutral density filters, spectral filters, shutters, apertures, beam stops, etc. associated with system 200.

Method Examples

Figure 3:
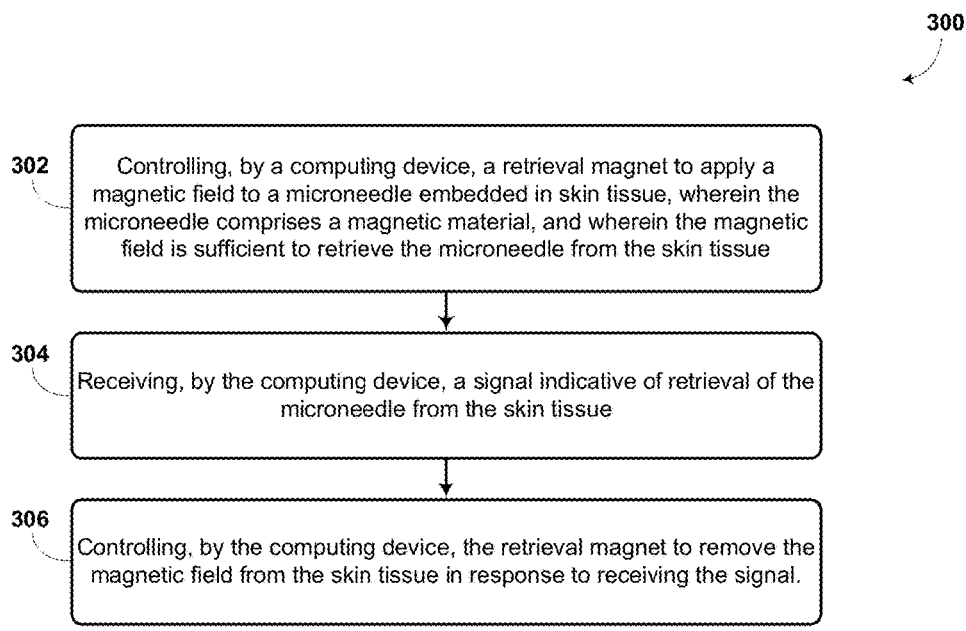
FIG. 3 illustrates a method, according to an example embodiment.

FIG. 3 illustrates a method 300, according to an embodiment. The method 300 includes blocks that may be carried out in any order. Furthermore, various blocks may be added to or subtracted from method 300 within the intended scope of this disclosure. The method 300 may correspond to steps that may be carried out using any or all of the systems illustrated and described in reference to FIGS. 1A-1G and FIG. 2.

Block 302 includes controlling, by a computing device, a retrieval magnet to apply a magnetic field to a microneedle embedded in skin tissue. The microneedle includes a magnetic material and the magnetic field may be sufficient to retrieve the microneedle from the skin tissue. The computing device referred to in block 302 may include controller 184 and/or controller 210 described in reference to FIGS. 1F-G and FIG. 2.

Block 304 includes receiving, by the computing device, a signal indicative of retrieval of the microneedle from the skin tissue. As described above, the signal may include an image of emission light (or lack thereof) that indicates the microneedles have been retrieved. For example, an excitation light source may illuminate a receiving surface of the retrieval magnet. A light sensor may be configured to sense light at an emission wavelength of the fluorophore. An image may be captured by a light sensor. Based on the image, a determination may be made by the computing device that the microneedles have been retrieved. For example, the image may indicate emission from each of the microneedles. In an alternate example, an object recognition analysis may be performed on the image to identify the microneedles, for instance, by their shape. Alternatively, the signal may include a change in magnetic susceptibility while the retrieval magnet is applying the magnetic field to the skin tissue. The change in magnetic susceptibility may indicate that one or more microneedles have been retrieved.

Block 306 includes the computing device controlling the retrieval magnet to remove the magnetic field from the skin tissue in response to receiving the signal. That is, in response to determining that the microneedles have been retrieved, the retrieval magnet may be shut off and/or the magnetic field may be removed from the skin tissue.

Figure 4:
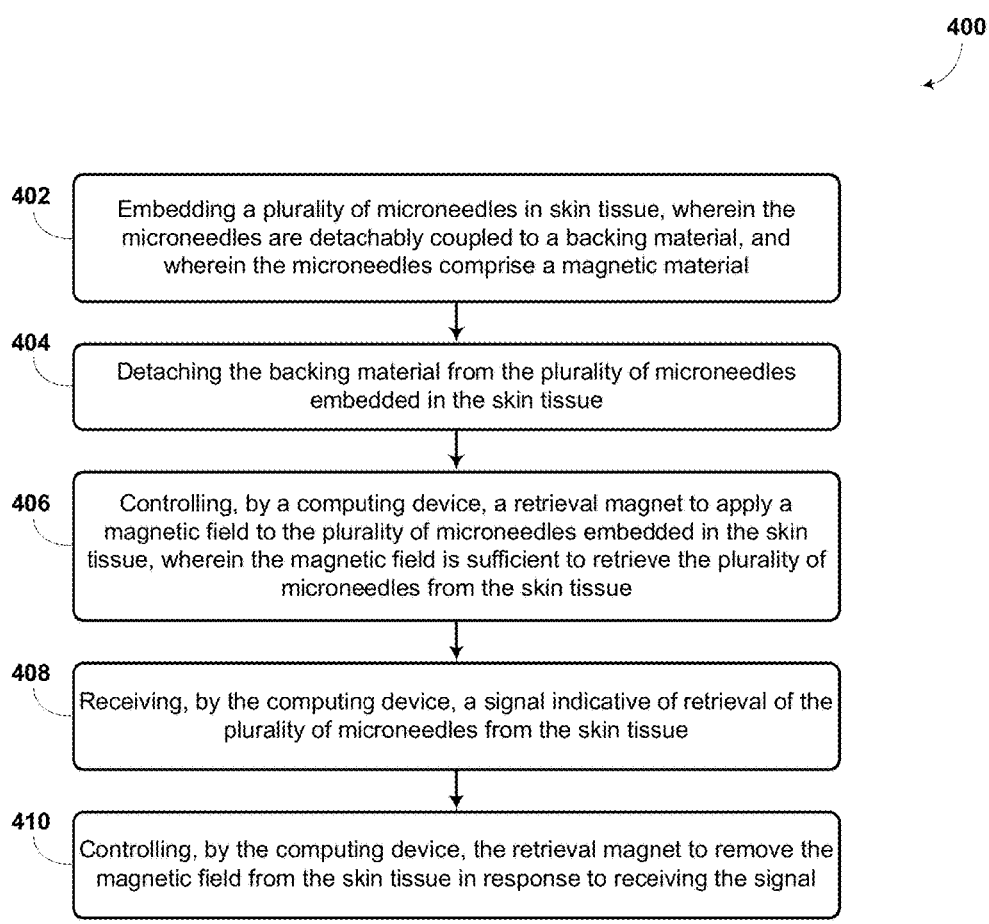
FIG. 4 illustrates a method, according to an example embodiment.

FIG. 4 illustrates a method 400, according to an embodiment. The method 400 includes blocks that may be carried out in any order. Furthermore, various blocks may be added to or subtracted from method 400 within the intended scope of this disclosure. The method 400 may correspond to steps that may be carried out using some or all of the elements of the systems described above and as illustrated in FIGS. 1A-1G and FIG. 2.

Block 402 includes embedding a plurality of microneedles in skin tissue. The microneedles are detachably coupled to a backing material and the microneedles include a magnetic material. Embedding the plurality of microneedles into the skin tissue may include positioning the backing material over an appropriate skin tissue area and thereafter applying pressure to the back of the backing material so as to push the plurality of microneedles into the skin tissue.

Block 404 includes detaching the backing material from the plurality of microneedles embedded in the skin tissue. Detaching the backing material from the plurality of microneedles may include peeling the backing material away from a base portion of the microneedles. Other ways of detaching the backing material are possible. For example, the backing material may be dissolved using water or alcohol.

Block 406 includes controlling, by a computing device, a retrieval magnet to apply a magnetic field to the plurality of microneedles embedded in the skin tissue, wherein the magnetic field is sufficient to retrieve the plurality of microneedles from the skin tissue. As contemplated herein, the computing device may include a controller. The controller may be a computer that includes a processor and a memory. The controller may be communicatively coupled to the retrieval magnet. In an example embodiment, the retrieval magnet may be an electromagnet and the controller may cause the retrieval magnet to apply the magnetic field by turning on the electromagnet.

Block 408 includes receiving, by the computing device, a signal indicative of retrieval of the plurality of microneedles from the skin tissue. As described above, the signal indicative of retrieval may include an image, an electrical signal, a magnetic signal, an optical signal, or a different type of signal corresponding to the microneedles being retrieved from the skin tissue.

Block 410 includes controlling, by the computing device, the retrieval magnet to remove the magnetic field from the skin tissue in response to receiving the signal. In other words, in response to receiving the signal indicative of microneedle retrieval, the computing device may shut off and/or remove the magnetic field from the skin tissue. This may involve turning off an electromagnet and/or physically moving the retrieval magnet away from the skin tissue.

The method may optionally include modulating a magnetic field proximate to the fluorophore. Namely, a fluorescence property of the fluorophore may vary based the magnetic field, among other factors. In other words, modulating the magnetic field in an environment of the fluorophore may change the fluorescence response of the fluorophore. In such a scenario, the magnetic field may be modulated at a given frequency or with a specific intensity/duration pattern. Under such conditions, the emission of the fluorophore may be modulated. Such modulation may improve performance of the microneedle system. For example, a signal to noise ratio may be improved by using the magnetic field modulation as a carrier wave with a homodyne or heterodyne amplification method. Other advantages to modulating the magnetic field proximate to the microneedles are contemplated herein.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

While various examples and embodiments have been disclosed, other examples and embodiments will be apparent to those skilled in the art. The various disclosed examples and embodiments are for purposes of illustration and are not intended to be limiting, with the true scope and spirit being indicated by the following claims.

What is claimed is:

1. A system comprising:
   a microneedle having a tip portion and a base portion, wherein the microneedle is configured to be embedded in skin tissue such that at least the tip portion is disposed beneath a surface of the skin, and wherein the microneedle is at least partially formed from a magnetic material;
   a retrieval magnet;
   a light sensor;
   a controller comprising at least one processor and programmed to carry out operations, the operations comprising:
   after the microneedle is embedded in the skin tissue, causing the retrieval magnet to apply a magnetic field to the magnetic material of the microneedle embedded in the skin tissue, wherein the magnetic field is sufficient to retrieve the microneedle from the skin tissue;
   receiving, from the light sensor, a signal indicative of retrieval of the microneedle from the skin tissue; and
   controlling the retrieval magnet to remove the applied magnetic field in response to receiving the signal from the light sensor.

2. The system of claim 1, wherein at least a portion of the magnetic material is incorporated into the base portion.

3. The system of claim 1, further comprising a sensing magnet, wherein the operations further comprise receiving a sensing signal based on an interaction between the sensing magnet and the magnetic material of the microneedle.

4. The system of claim 1, wherein the microneedle comprises a hydrogel matrix and wherein the magnetic material is disposed in the hydrogel matrix.

5. The system of claim 1, wherein the magnetic material comprises magnetic nanoparticles.

6. The system of claim 1, wherein the magnetic material comprises at least one material selected from the group consisting of iron oxide, ferrite, alnico, nickel, and rare earth material.

7. The system of claim 1, further comprising a backing material detachably coupled to the microneedle.

8. The system of claim 1, wherein the microneedle further comprises a fluorophore and wherein the signal is based on the light sensor sensing fluorescence light emitted by the fluorophore.

9. The system of claim 8, further comprising a light source, wherein the operations further include operating the light source to emit light at an excitation wavelength of the fluorophore, and wherein the fluorescence light emitted by the fluorophore is emitted in response to illumination by the light source.

10. The system of claim 1, wherein the microneedle is further configured to produce or modulate a local magnetic field within the skin tissue.

11. A method comprising:
    controlling, by a controller, a retrieval magnet to apply a magnetic field to a magnetic material of a microneedle embedded in skin tissue such that a tip portion of the microneedle is disposed beneath a surface of the skin, wherein the microneedle is at least partially formed from the magnetic material that is disposed within the tip portion, and wherein the magnetic field is sufficient to retrieve the microneedle from the skin tissue;
    receiving, by the controller from a light sensor, a signal indicative of retrieval of the microneedle from the skin tissue; and
    controlling, by the controller, the retrieval magnet to remove the applied magnetic field in response to receiving the signal from the light sensor.

12. The method of claim 11, wherein the microneedle additionally comprises a base portion, and wherein at least a portion of the magnetic material is incorporated into the base portion.

13. The method of claim 11, wherein the microneedle comprises a hydrogel matrix, and wherein the magnetic material is disposed in the hydrogel matrix.

14. The method of claim 11, further comprising:
embedding the microneedle in the skin tissue.

15. The method of claim 14, further comprising:
after embedding the microneedle in the skin tissue, removing a backing material from the microneedle.

16. The method of claim 11, wherein the magnetic material comprises at least one material selected from the group consisting of iron oxide, ferrite, alnico, nickel, and rare earth material.

17. The method of claim 11, wherein the microneedle further comprises a fluorophore, and wherein the signal is based on the light sensor sensing fluorescence light emitted by the fluorophore.

18. The method of claim 17, further comprising emitting light at an excitation wavelength of the fluorophore, wherein the fluorescence light emitted by the fluorophore is emitted in response to being illuminated by the emitted light.

19. A method comprising:
embedding a plurality of microneedles in skin tissue such that a respective tip portion of each microneedle is disposed beneath a surface of the skin, wherein the microneedles are detachably coupled to a backing material, and wherein the microneedles are at least partially formed from a magnetic material;
detaching the backing material from the plurality of microneedles embedded in the skin tissue;
controlling, by a controller, a retrieval magnet to apply a magnetic field to the magnetic material of the plurality of microneedles embedded in the skin tissue, wherein the magnetic field is sufficient to retrieve the plurality of microneedles from the skin tissue;
receiving, by the controller from a light sensor, a signal indicative of retrieval of the plurality of microneedles from the skin tissue; and
controlling, by the controller, the retrieval magnet to remove the applied magnetic field in response to receiving the signal from the light sensor.

20. The method of claim 19, wherein each of the plurality of microneedles additionally comprises a base portion and wherein at least a portion of the magnetic material is incorporated into the base portion.

21. The method of claim 19, wherein each of the plurality of microneedles comprises a hydrogel matrix and wherein the magnetic material is disposed in the hydrogel matrix.

22. The method of claim 19, wherein the magnetic material comprises at least one material selected from the group consisting of iron oxide, ferrite, alnico, nickel, and rare earth material.

23. The method of claim 19, wherein the plurality of microneedles further comprises a fluorophore, and wherein the signal is based on the light sensor sensing fluorescence light emitted by the fluorophore.

24. The method of claim 23, further comprising modulating a magnetic field proximate to the fluorophore, wherein a fluorescence property of the fluorophore varies based on the magnetic field.

25. The method of claim 23, further comprising emitting light at an excitation wavelength of the fluorophore, wherein the fluorescence light emitted by the fluorophore is emitted in response to being illuminated by the emitted light.

* * * * *